United States Patent [19]

Lander

[11] Patent Number: 5,053,016
[45] Date of Patent: Oct. 1, 1991

[54] VALVE SEAT FOR AN INSUFFLATION CANNULA ASSEMBLY

[75] Inventor: Jack R. Lander, Danbury, Conn.

[73] Assignee: United States Surgical Corporation, Norwalk, Conn.

[21] Appl. No.: 488,628

[22] Filed: Mar. 2, 1990

Related U.S. Application Data

[63] Continuation of Ser. No. 140,025, Dec. 31, 1987, Pat. No. 4,943,280.

[51] Int. Cl.⁵ .............................................. A61M 5/18
[52] U.S. Cl. ................................... 604/169; 251/298
[58] Field of Search ............... 604/158, 164, 165, 167, 604/171, 272–274; 251/298

[56] References Cited

U.S. PATENT DOCUMENTS

| | | | |
|---|---|---|---|
| 1,089,805 | 3/1914 | Wolf | 604/169 |
| 1,856,138 | 5/1932 | Ruemelin | 251/298 |
| 2,660,396 | 11/1953 | Heagerty | 251/298 |
| 3,053,278 | 9/1962 | Verheul | 137/614.21 |
| 3,994,287 | 11/1976 | Turp et al. | 128/6 |
| 4,000,739 | 1/1977 | Stevens | 604/280 |
| 4,033,549 | 7/1977 | Stamer | 251/298 |
| 4,177,814 | 12/1979 | Knepshield et al. | 128/348 |
| 4,373,550 | 2/1983 | Yelich | 251/364 |
| 4,379,458 | 4/1983 | Bauer et al. | 604/264 |
| 4,477,053 | 10/1984 | Jandrasi | 251/86 |
| 4,535,773 | 8/1985 | Yoon | 604/51 |
| 4,601,710 | 7/1986 | Moll | 604/165 |
| 4,654,030 | 3/1987 | Moll et al. | 604/165 |

FOREIGN PATENT DOCUMENTS 1482857 8/1977 United Kingdom .

Primary Examiner—Max Hindenburg
Attorney, Agent, or Firm—Thomas R. Bremer

[57] ABSTRACT

A cannula assembly for use in conjunction with insufflatory surgical techniques includes a cannula, a housing mounted on one end of the cannula, and a flapper valve mounted in the housing. The flapper valve includes a valve seat which is situated at an opening formed in the housing, a valve plug which is adapted to engage the valve seat to form a substantially gas tight seal with the valve seat, and a support plate on which the valve plug is mounted and which is biased to pivot the plug into and out of engagement with the valve seat. The valve plug is movable on the support plate so as to be self-aligning with the valve seat when the plug and valve are in engagement.

8 Claims, 4 Drawing Sheets

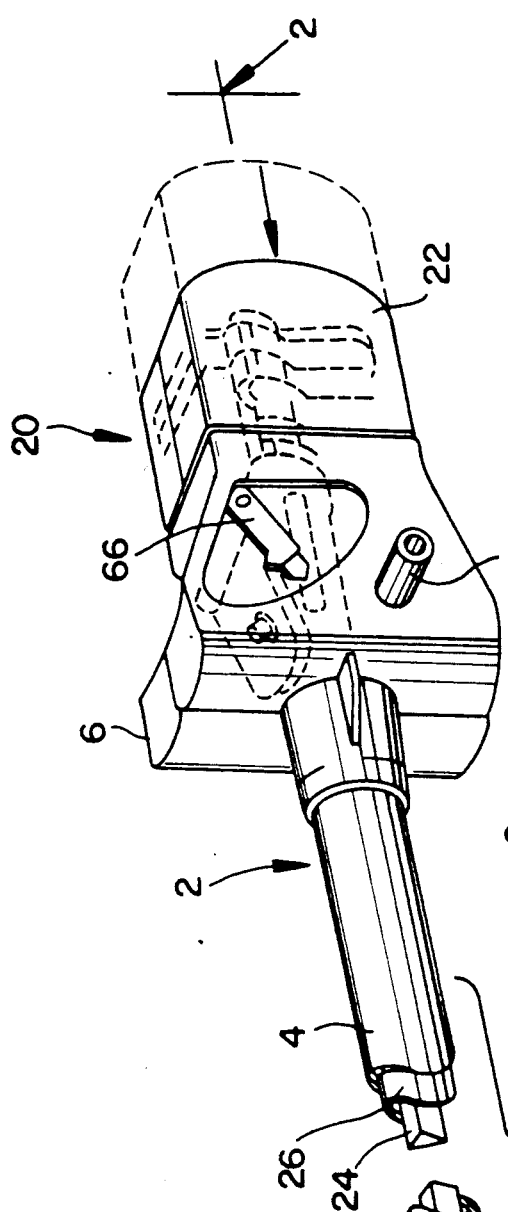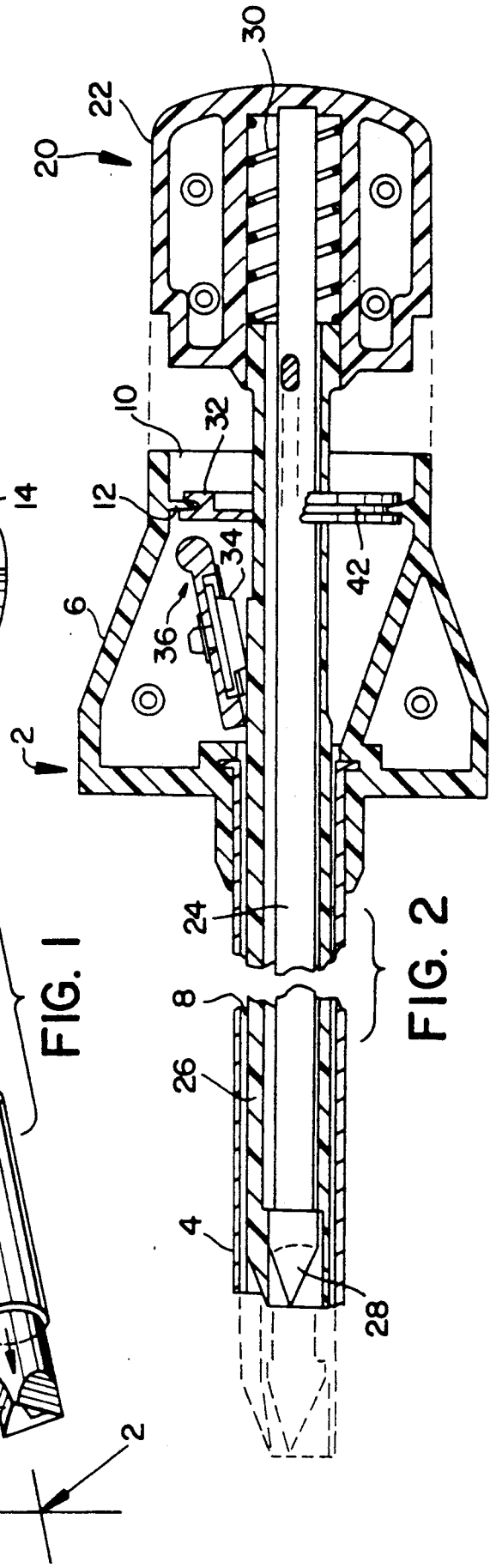

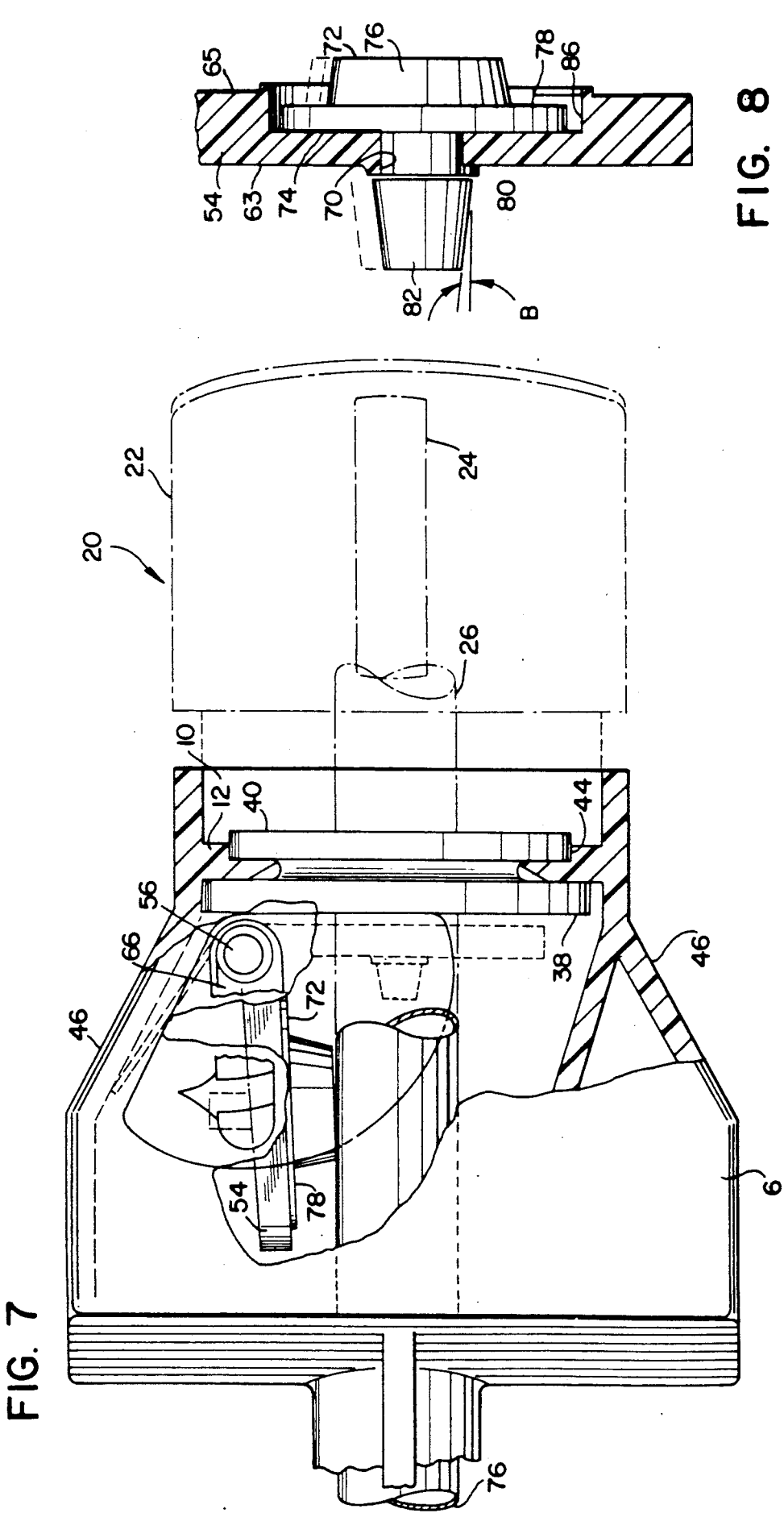

VALVE SEAT FOR AN INSUFFLATION CANNULA ASSEMBLY

This application is a continuation of copending application Ser. No. 07/140,025 filed Dec. 31, 1987, U.S. Pat. No. 4,943,280.

BACKGROUND OF THE INVENTION

1. Field Of The Invention

The present invention relates to an insufflation cannula assembly adapted to receive a trocar, endoscope or other surgical instrument and for use in conjunction with insufflatory surgical techniques, and more particularly relates to a valve used in the assembly for maintaining insufflation pressure in a body cavity.

2. Description of the Prior Art

Insufflatory surgery involves filling a body cavity with a pressurized gas to maintain the cavity under a certain predetermined pressure. One way of performing the surgery is by first puncturing the skin in a desired body cavity region with a needle. The needle includes a stylet which introduces an insufflation gas into the body cavity to inflate it.

A trocar is then used to puncture the body cavity. The trocar is inserted through a cannula or sheath, which cannula partially enters the body cavity through the incision made by the trocar. The trocar may then be removed from the cannula, and an elongated endoscope may be inserted through the cannula to view the anatomical cavity.

Various types of cannula or trocar assemblies are provided with valves for maintaining a certain gas pressure in the cavity when the trocar or other surgical instrument is removed from the cannula.

For example, U.S. Pat. No. 4,654,030, which issued to Frederic Moll et al., and copending U.S. application Ser. No. 920,509, filed Oct. 17, 1986, disclose a trocar assembly having a cannula and employing a flapper valve to close off the cannula passage after the trocar or other instrument has been withdrawn.

As shown in FIG. 7 of the Moll et al. patent, the flapper valve includes a U-shaped flapper 82 and a grommet 77 formed with a central opening 78 through which the trocar may be inserted or withdrawn. The flapper carries a circular pad 87, and is spring-biased so that the pad engages grommet 77 and forms a seal with the grommet.

Although the flapper valve disclosed in the Moll et al. patent works well in most applications to maintain pressure in the body cavity, there are certain inherent drawbacks in its design.

First, the circular pad is rigidly mounted on the flapper so that it cannot move with respect to the flapper. If the pad and grommet are slightly out of alignment when the valve closes, the pad may not seat properly on the grommet, and insufflating gas may leak from the body cavity through the valve.

Second, the circular pad is made of a deformable material such as Tygon (TM), and is formed by a molding process. Irregularities in the pad's grommet-engaging surface due to shrinkage of the pad material during its formation may provide leakage paths through the valve. Also, the pad bears with considerable spring pressure on the side of the trocar when the trocar is inserted into the cannula through the valve. A depression may form in the pad's surface which may cause further leakage when the valve closes.

Third, the circular pad is relatively flat or has a slight curvature. It engages protruding lips 88 formed on the grommet, which lips surround the grommet opening 78. With this structure, the flapper valve disclosed in the Moll et al. patent provides minimal contact area between the pad and the grommet, and any slight irregularity in one or the other may cause the valve to leak.

OBJECTS AND SUMMARY OF THE INVENTION

It is an object of the present invention to provide a valve for an insufflation cannula assembly which minimizes fluid leakage through the cannula.

It is another object of the present invention to provide a flapper valve whose sealing members automatically align with each other when the valve closes to provide an enhanced gas tight seal.

It is a further object of the present invention to provide a flapper valve whose sealing members contact each other over a greater surface area.

It is yet another object of the present invention to provide an insufflation cannula assembly for use with a trocar, endoscope or other surgical instrument, which cannula assembly provides negligible or no gas leakage.

It is a still further object of the present invention to provide a flapper valve which is an improvement over the flapper valve disclosed in Moll et al. U.S. Pat. No. 4,654,030.

In one form of the present invention, a cannula assembly for use in conjunction with insufflatory surgical techniques includes a cannula having opposite open ends, a housing mounted on one end of the cannula and having an opening formed in the housing, and a flapper valve mounted in the housing to seal the cannula passage when a surgical instrument, such as a trocar, endoscope or the like, is withdrawn from the cannula.

The flapper valve basically includes a valve seat situated at the housing opening, a valve plug which engages the valve seat and forms a substantially fluidtight seal with the seat, and a support plate and spring mechanism for mounting the valve plug in the housing and for pivoting the plug into and out of engagement with the valve seat.

The valve seat has an opening formed through its thickness, which opening is in communication with the cannula passage. The valve seat is positioned in the housing such that its opening is co-axial with the cannula so that a surgical instrument, such as a trocar or endoscope, may be inserted through the valve seat opening and into the cannula passage.

The valve plug is mounted loosely but securely on the support plate so that it can move radially on a surface of the support plate and align itself with the opening formed in the valve seat when the two engage each other. The surface of the valve plug which engages the valve seat has a frusto-conical shape so that the surface is partially received by the valve seat opening when the valve closes.

The support plate is basically a U-shaped member which extends from the radial side of an upstanding post mounted in the housing. A helical spring mounted co-axially on the post engages the housing and the support plate and biases the valve plug into engagement with the valve seat. A trocar or other surgical instrument inserted through the valve seat opening will cause the valve plug to pivot away from the valve seat and out of the trocar's axial path of travel between the valve seat opening and the cannula passage.

Preferred forms of the flapper valve and insufflation cannula assembly, as well as other embodiments, objects, features and advantages of this invention, will be apparent from the following detailed description of illustrative embodiments thereof, which is to be read in connection with the accompanying drawings.

BRIEF DESCRIPTION OF THE DRAWINGS

FIG. 1 is an isometric view of the cannula assembly of the present invention with a trocar assembly mounted thereon.

FIG. 2 is a sectional view of the cannula assembly and trocar assembly shown in FIG. 1, taken along line 2—2 of FIG. 1.

FIG. 7 is a top view of the cannula assembly with its housing partially broken away.

FIG. 8 is an enlarged, detailed view of a portion of the flapper valve of the present invention.

DETAILED DESCRIPTION OF THE PREFERRED EMBODIMENTS

Figure 3:
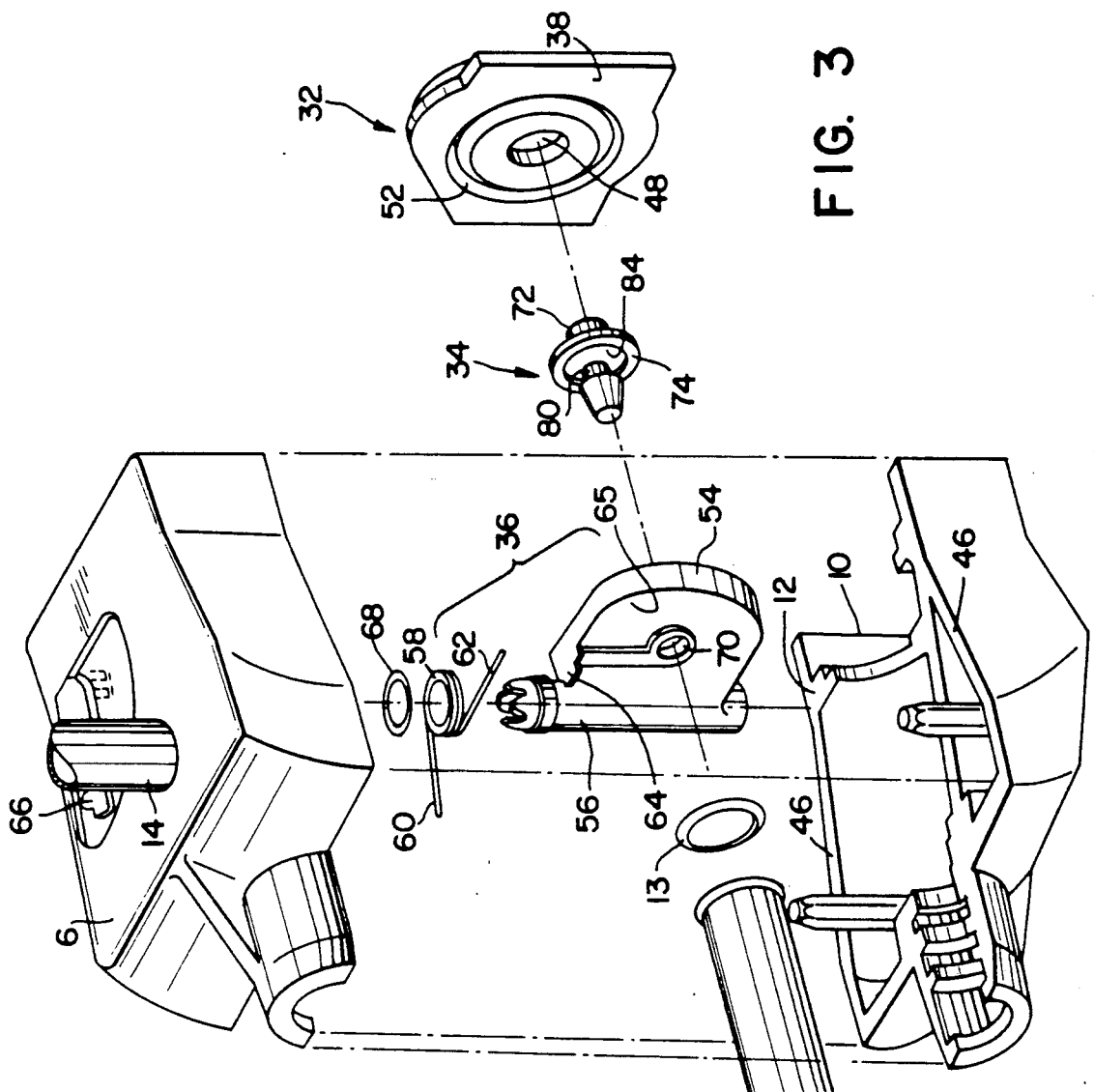
FIG. 3 is an exploded view of the cannula assembly of the present invention.

Referring initially to FIGS. 1 and 2 of the drawings, it will be seen that a cannula assembly 2 used in connection with insufflatory surgical techniques basically includes a cannula 4 and a housing 6 mounted on one end of the cannula 4. The cannula 4 is formed as an elongated sleeve having opposite proximate and distal open ends, and thus defines a cannula passage 8 in its interior. The cannula 4 may be formed from a stainless steel or other rigid material.

The housing 6 of the cannula assembly is rigidly secured to the proximate end of the cannula 4. It has an open interior for mounting other components of the cannula assembly, and has a rear opening 10 defined by a circular flange 12 extending inwardly of the housing, which opening 10 is situated co-axially with the cannula 4. An O-ring 13 (see FIG. 3) may be mounted on the cannula 4 to prevent leakage between the cannula and the housing. Additionally, the housing 6 includes a stopcock port 14 into which the nozzle of a stopcock 16 is inserted (see FIG. 4), the port 14 being provided for passing additional insufflating gas into the body cavity.

The cannula assembly 2, with its cannula 4 and its housing 6, is adapted to receive a surgical instrument through the opening 10 in its housing. An example of such an instrument is the trocar assembly 20 shown in FIGS. 1 and 2 of the drawings, the trocar assembly 20 being mounted on the rear side of the housing 6.

The trocar assembly 20 basically includes a hand grip portion or head 22, an obturator 24 mounted on the head 22 of the trocar assembly and extending outwardly from the head, and an obturator shield 26 which houses the obturator 24. The obturator 24 is formed with a piercing tip 28 for puncturing the body cavity. A spring 30 in the head 22 of the trocar assembly biases the shield 26 axially away from the head so that it covers the obturator tip 28.

The trocar assembly 20 is mounted on the cannula assembly 2 so that its obturator 24 and shield 26 are slidably received in the cannula passage 8 with the obturator shield extending beyond the distal end of the cannula 4.

In operation, the distal end of the cannula/trocar assembly is placed against the skin at the body cavity region, and pressure is exerted on the assembly against the skin. This pressure causes the obturator shield 26 to be pushed rearwardly against the force of the spring 30 to a retracted position, thereby exposing the piercing tip 28 of the obturator. The tip enters the skin and underlying tissue with continued pressure. Once the tip has penetrated the tissue and has entered the cavity, the force against the distal end of the shield 26 ceases and the shield is automatically moved axially forward to its extended position covering the tip 28 through the action of the spring 30.

A more detailed description of the trocar assembly described herein, and its operation, is provided in Moll et al. U.S. Pat. No. 4,654,030, which is incorporated herein by reference.

Figure 4:
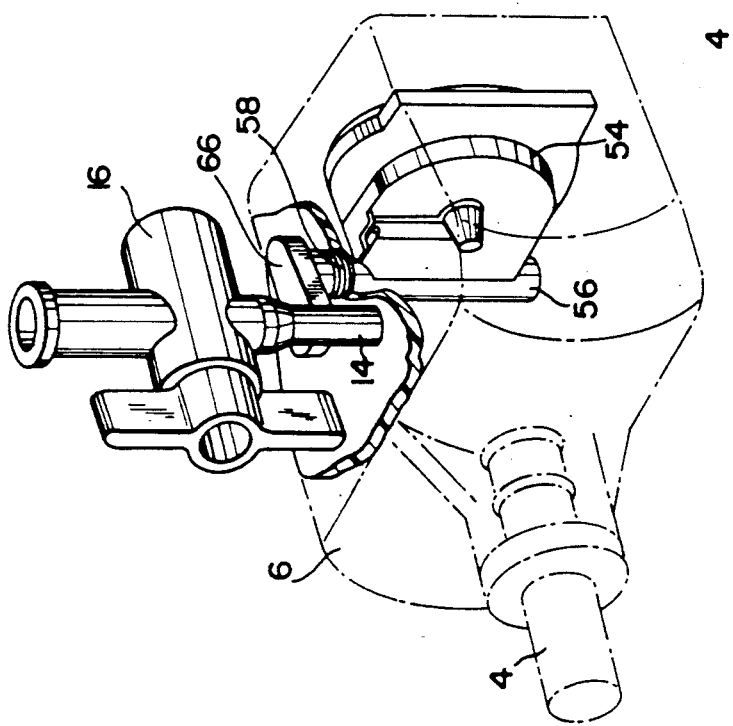
FIG. 4 is an isometric view of the cannula assembly shown in FIG. 3 with its housing partially broken away.
Figure 6:
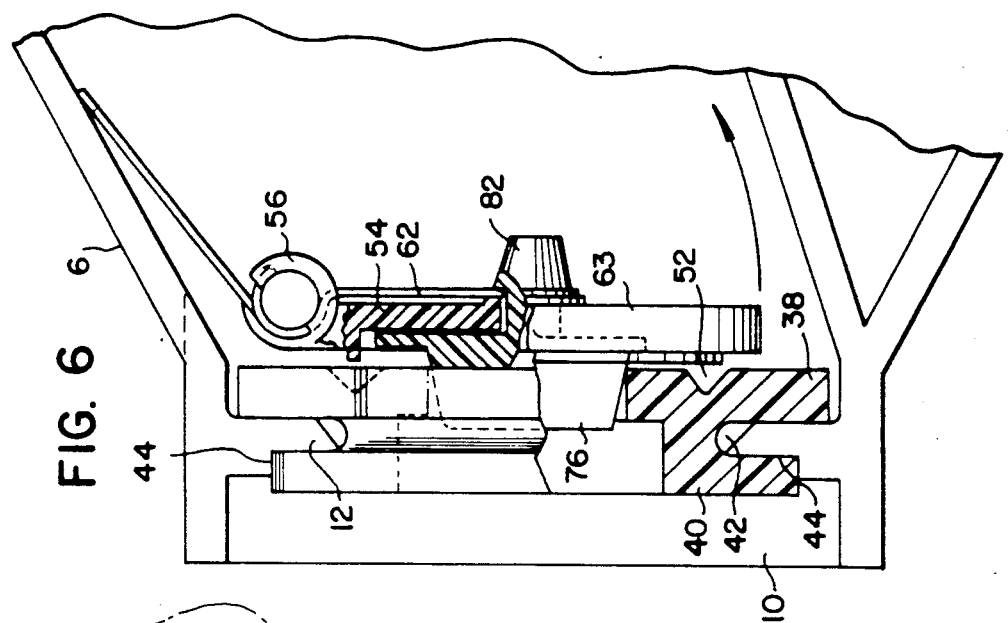
FIG. 6 is a partial sectional view of the flapper valve used in the cannula assembly of the present invention.
Figure 5:
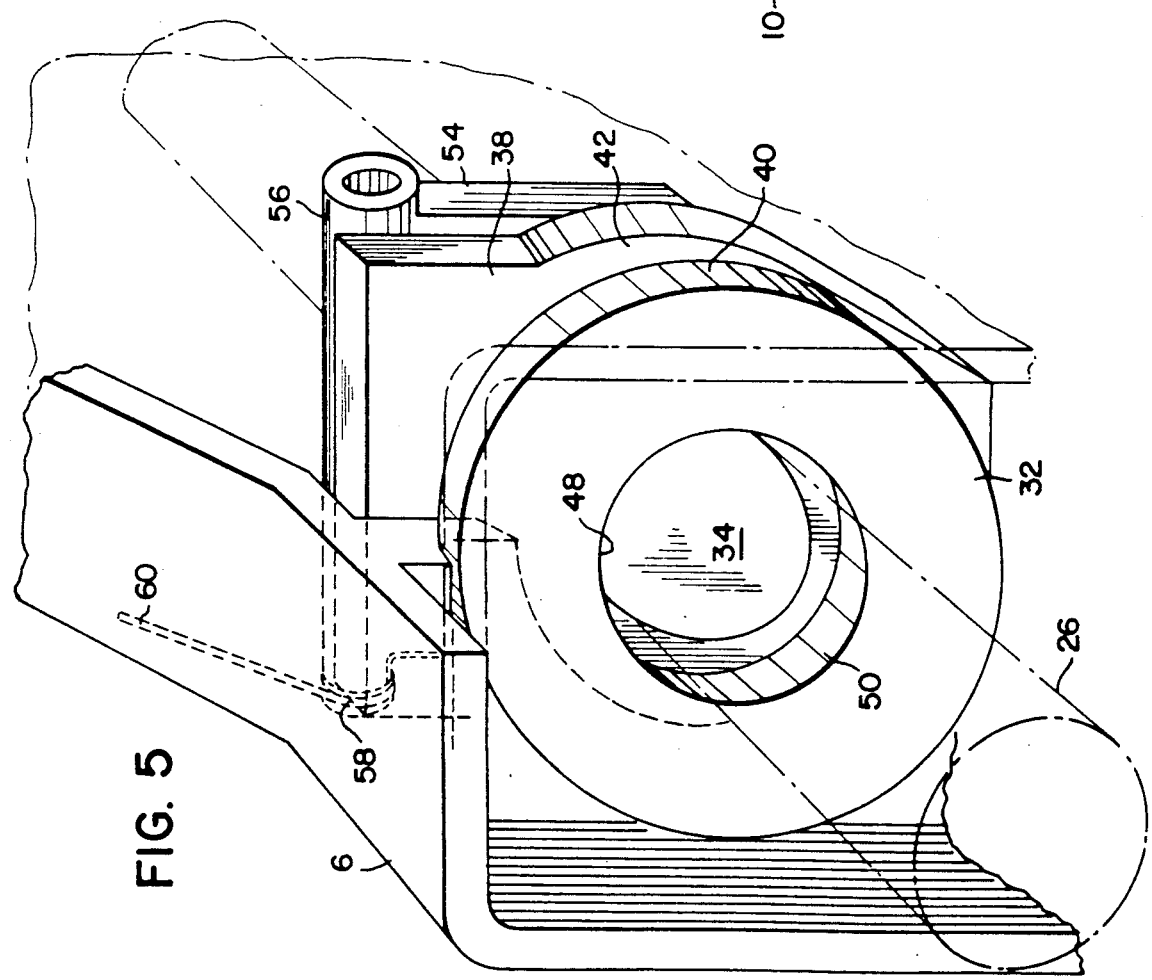
FIG. 5 is a rear perspective view of a portion of the cannula assembly.

As is provided in the device disclosed in the above-identified Moll et al. patent, the cannula assembly 2 of the present invention includes a flapper valve which opens to allow a surgical instrument, such as the trocar assembly 20, to be inserted through the cannula 4, and closes when the surgical instrument has been withdrawn, in order to maintain gas pressure in the body cavity which has been inflated with an insufflation gas. The flapper valve of the present invention as shown in FIG. 3 basically includes three components: a valve seat 32, a valve plug 34 which engages the valve seat 32, and a mechanism 36 for mounting the valve plug 34 and for pivoting the plug into and out of engagement with the valve seat 32.

As shown in FIGS. 3 through 8 of the drawings, the valve seat 32 is mounted in the circular flange 12 at the rear opening 10 formed in the housing 6 of the cannula assembly. The seat 32 basically includes a forward portion 38 and a rearward portion 40 which are interconnected and which define a recess 42 between them, which recess 42 receives the circular flange 12 of the housing. The rearward portion 40 is preferably circular, and is received in a recess 44 formed in the circular flange 12.

The forward portion 38 is substantially rectangular, and has a greater transverse width than the diameter of the circular rearward portion 40 so that it extends substantially to the opposite lateral sides 46 of the housing 6. The forward and rearward portions 38, 40 contact the sides of the flange over an area sufficient to prevent leakage.

The valve seat 32 includes an opening 48 formed centrally through its thickness. The valve seat 32 is situated in the housing 6 so that its opening 48 is co-axial with the cannula 4 and is in communication with the cannula passage 8 through the interior of the housing; this will allow a surgical instrument, such as the trocar assembly 20 shown in FIGS. 1 and 2, or an endoscope, for example, to pass through the valve seat opening 48 and into the cannula passage 8 from the rear side of the cannula assembly housing 6.

A portion of the valve seat 32 surrounding the opening is reduced in thickness. This portion is defined by a circular recess 50 formed in the rearward portion 40 of the valve seat, and a recessed groove 52 formed in the surface of the forward portion 38 of the valve seat and concentrically surrounding the opening 48.

The valve seat 32 is formed from a rubber or other elastic material. As will be seen, because of the elasticity of the material from which it is formed and the reduced thickness of the area surrounding the opening 48, the valve seat 32 will deform to accommodate the valve plug 34 and thereby conform to the shape of the valve plug 34 when the two engage each other, with substantial areas of the two being in contact so as to form a substantially gas tight seal. Also, the reduced thickness portion at 50 and 52 surrounding the valve seat opening 48 allows the valve seat 32 to expand and closely engage the obturator shield 26 of the trocar assembly 20 or other surgical instrument inserted in the cannula assembly, and to prevent fluid from escaping from the body cavity.

As mentioned previously, the flapper valve also includes a mechanism 36 for mounting the valve plug 34 and for pivoting the valve plug into and out of engagement with the valve seat 32. As shown in FIG. 3 of the drawings, such a mechanism includes a support plate 54 which is preferably U-shaped. The support plate 54 extends outwardly from a radial side of an upstanding post 56 mounted in the housing 6 of the cannula assembly.

A tensioned helical spring 58 is co-axially mounted on the post 56, and includes two ends 60, 62. One end 60 bears against a side 46 of the cannula housing 6, and the other end 62 bears against the rear side 63 of the support plate below a tab 64 extending outwardly from the rear side, which tab 64 keeps the spring end in place. The spring 58 biases the support plate 54 such that the valve plug 34 mounted on the plate will engage the valve seat 32 to affect a gas tight seal.

When a trocar or other surgical instrument is inserted through the valve seat opening 48 into the housing 6 of the cannula assembly, it will engage the valve plug 34 and cause the support plate 54 to pivot against the force of the spring 58 towards the side 46 of the housing so that the valve plug 34 is out of engagement with the valve seat 32. This opens the valve and allows the surgical instrument to be inserted through the interior of the cannula assembly housing 6 and into the cannula 4. When the trocar or surgical instrument is withdrawn, the support plate 54 is spring biased to pivot so that the valve plug 34 will automatically engage the valve seat 32, thereby closing the valve.

A lever 66 is provided on the outside of the housing 6. The lever 66 is mounted to the upstanding post 56 and pivots with the post. The lever 66 is provided for the surgeon to manipulate so that the valve can be manually opened to desufflate the body cavity. To ensure fluid-tightness, an O-ring 68 is mounted on the post between the spring 58 and the lever 66.

The support plate 54 also has an opening 70 formed through its thickness, that is, between its rear and front sides 63, 65. As will be seen, the opening 70 is provided for mounting the valve plug 34 to the support plate.

As seen in FIG. 8, the valve plug 34 of the flapper valve basically includes a front face 72 and a rear face 74 opposite the front face. A portion 76 of the front face is formed with a conical shape, and more preferably, a frusto-conical shape. The conically-shaped portion 76 of the valve plug is preferably sloped inwardly on its sides at an angle A of about 30°.

The front face 72 of the valve plug is also formed with a flange 78 which surrounds the conically-shaped portion 76. Flange 78 acts to ensure that the tip of shield 26 of the trocar assembly, or other surgical instrument which may be inserted, is guided into the cannula 4 and does not momentarily get hung up at the joint formed by valve plug 34 and support plate 54.

As mentioned previously, the valve plug 34 is mounted on the support plate 54 and pivots with the support plate into and out of engagement with the valve seat 32. One of the important features of the flapper valve of the present invention which distinguishes it from the valve employed in the trocar disclosed in U.S. Pat. No. 4,654,030 (Moll et al.) is that the valve plug 34 is loosely but securely mounted on the support plate 54 so that it can move radially to a certain extent on the front face of the support plate. The ability of the plug 34 to move with respect to the support plate 54 and the particular shape of the valve plug (i.e., conical or frusto-conical) provide the valve plug with a self-seating capability which allows it to automatically align itself with the valve seat 32 when the two engage.

A stem portion 80 extends outwardly from the rear face 74 of the valve plug 34. As will be seen, the stem portion 80 is provided for mounting the valve plug 34 to the support plate 54, and for providing the valve plug with a degree of radial movement on the front side of the support plate.

The stem portion 80 may include a free end on which is mounted a retaining head 82. Additionally, the retaining head 82 may form the free end of the stem portion 80. The retaining head 82 in its preferred form is also frusto-conically shaped with sides that converge in a direction away from the rear side 63 of the support plate, preferably sloping inwardly at an angle B of about 20°.

The valve plug 34 is mounted on the support plate 54 with its conically-shaped front face 72 and its retaining head 82 disposed on opposite front and rear sides 65, 63 of the support plate, respectively, and with its stem portion 80 received by the support plate opening 70.

The retaining head 82 is made oversized, that is, with a diameter that is greater than that of the support plate opening 70, to securely connect the valve plug 34 to the support plate 54. However, the stem portion 80 of the valve plug is formed with a diameter that is less than that of the support plate opening 70. Thus, when mounted on the support plate 54, the valve plug 34 is free to move in any radial direction on the front side 65 of the support plate, and is limited in its radial movement by the difference between the diameters of the support plate opening 70 and the stem portion 80.

For example, if the support plate opening 70 is formed with a diameter of 0.127 inches and the valve plug stem portion 80 is formed with a diameter of 0.095 inches, then the valve plug will be able to travel 0.016 inches from the center of the support plate opening in any radial direction.

The valve plug 34 is thus free to "float" on the surface of the support plate 54 in any radial direction, and to align itself with the central opening 48 formed in the valve seat 32. When the valve closes, the engagement of the valve seat 32 with the frusto-conical front face of the valve plug 34 forces the valve plug into proper alignment with the valve seat to effect a gas tight seal.

The rear face 74 of the valve plug 34 is also formed with a recessed portion 84 concentrically surrounding the stem portion 80. This recessed portion 84 is provided basically for two reasons. First, it provides the plug with less surface area on its rear face 73 to contact the front side 65 of the support plate. This reduces the drag or friction between the two and allows free movement of the valve plug 34 on the support plate 54.

Second, if desired, the recessed portion 84 may serve to receive a silicone grease or other lubricant to lubricate the interface between the valve plug and the support plate, which also minimizes friction between the two.

If desired, the front face 72 of the valve plug 34 may be formed from an inelastic material such as plastic, aluminum, stainless steel or the like. The retaining head 82 may be formed from the same or other material as the front face 72 of the valve plug and joined to the end of stem portion 80 after the stem portion has been mounted in the support plate opening 70, or may be formed from an elastic material and force-fitted through plate opening 70. The retaining head 82, formed of elastic material, can compress and then expand after its insertion through the support plate opening, and thereby return to an intentional interference.

The valve seat 32, being molded of rubber or other elastic material, conforms by stretching and compressing to the shape of the valve plug 34 when the valve plug is wedged in the valve seat opening 48. Thus, the valve seat surrounding the opening 48 can engage the valve plug 34 over substantially all of its entire thickness to form an effective gas tight seal.

The valve plug 34 may be mounted in a circular recess 86 (see FIG. 8) formed in the front side 65 of the support plate 54, the diameter of the circular recess 86 being made sufficiently large so as not to limit the radial movement of the valve plug on the support plate.

The flapper valve of the present invention provides an enhanced gas tight seal by its capability of being self-seating. More specifically, the frusto-conical shape of the valve plug 34 and its ability to "float" on the support plate 54 allow it to come into proper alignment with the valve seat 32 when the two engage. Furthermore, the configuration and elasticity of the valve seat 32 and the particular shape of the valve plug 34 permit the two to contact each other over a greater surface area, thus ensuring an effective seal.

Although the illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A flapper valve for an insufflation cannula assembly, the cannula assembly including a cannula defining a cannula passage and a housing mounted on one end of the cannula and having an opening formed therein, the flapper valve being mounted in the housing of the assembly, the flapper valve comprising:
   a valve seat within the housing opening, said valve seat being formed of a resilient flexible material and having an opening formed therein, said valve seat opening being bounded by a lip extending at least generally radially inwardly of said valve seat, at least a portion of said lip being of reduced thickness, said reduced thickness portion thereby being of greater flexibility than adjacent portions of said valve seat, said valve seat opening being in communication with the cannula passage and being adapted to allow a surgical instrument to pass therethrough and into the cannula passage;
   a valve plate pivotally mounted in said housing, said valve plate having front and back faces, said front face of said valve plate being dimensioned and adapted to engage said resilient flexible lip of said valve seat, said valve plate including means for obstructing said opening in said valve seat by engagement with said lip of said valve seat in a manner to cause said lip to become resiliently flexed to thereby affect a substantially gas tight seal; and
   biasing means for biasing said valve plate into engagement with said lip of said valve seat.

2. The flapper valve of claim 1, wherein said valve plate is substantially U-shaped.

3. The flapper valve of claim 1, wherein said valve seat engages and is maintained in position by a flange positioned within said housing.

4. The flapper valve of claim 3, wherein said valve seat engages said flange over an area sufficient to prevent gas leakage therebetween.

5. The flapper valve of claim 1, wherein said reduced thickness portion of said valve seat is adapted to conform to the shape of said obstructing means to form a substantially gas tight seal therewith.

6. A valve seat for use with a flapper valve assembly in an insufflation cannula assembly comprising:
   a valve seat body formed of a resilient flexible material having an opening formed therein, said valve seat opening being bounded by a lip, at least a portion of said lip being of reduced thickness and extending at least generally radially inwardly of said valve seat body, said reduced thickness portion thereby being of greater flexibility than adjacent portions of said valve seat;
   the flapper valve adapted to be moved from positions into and out of engagement at least with said reduced thickness portion of said valve seat, said flapper valve engaging said reduced thickness portion in a manner to cause said reduced thickness portion to become resiliently flexed to affect a substantially gas tight seal.

7. An insufflation cannula assembly comprising:
   a cannula having opposite end portions;
   a housing mounted at one end of the cannula, said housing having an opening formed therein;
   flange means positioned within said housing adjacent said housing opening;
   a valve seat positioned on said flange means, said valve seat having an opening formed therein, said valve seat opening being bounded by a resilient flexible lip, at least a portion of said lip being of reduced thickness and extending at least generally radially inwardly of said valve seat, said reduced thickness portion thereby being of greater flexibility than adjacent portions of said valve seat, said valve seat opening being in communication with the cannula passage and being adapted to allow a surgical instrument to pass therethrough and into the cannula passage;
   a valve plate pivotally mounted in said housing, said valve plate having front and back faces, said front face of said valve plate being dimensioned and adapted to engage said lip of said valve seat, said valve plate including means for obstructing said opening in said valve seat by engagement with said lip of said valve seat in a manner to cause said lip to become resiliently flexed to thereby affect a substantially gas tight seal; and
   biasing means for biasing said valve plate into engagement with said lip of said valve seat.

8. The insufflation cannula assembly of claim 7, wherein said lip of said valve seat is formed of a resilient material.

* * * * *